United States Patent [19]

Weikel

[11] 4,228,919
[45] Oct. 21, 1980

[54] DENTAL AMALGAM DISPENSER

[76] Inventor: Maurice M. Weikel, 1050 Greenfield Dr., El Cajon, Calif. 92021

[21] Appl. No.: 940,704

[22] Filed: Sep. 8, 1978

[51] Int. Cl.² .............................................. B65B 1/30
[52] U.S. Cl. ...................................... 221/96; 222/137; 222/145; 222/188; 222/307
[58] Field of Search ............... 222/139, 145, 136, 137, 222/305–308, 361, 188; 221/96, 133, 263, 264

[56] References Cited

U.S. PATENT DOCUMENTS

| | | | |
|---|---|---|---|
| 1,286,881 | 12/1918 | Gray | 222/145 |
| 3,111,959 | 11/1963 | Allen et al. | 222/188 |
| 3,168,213 | 2/1965 | De Gon | 221/96 |
| 3,521,793 | 7/1970 | McShirley | 222/308 |
| 4,139,030 | 2/1979 | Schroeder et al. | 221/96 |

*Primary Examiner*—H. Grant Skaggs
*Attorney, Agent, or Firm*—Fulwider, Patton, Rieber, Lee & Utecht

[57] ABSTRACT

A dental amalgam dispenser is provided with a housing having an integrally formed funnel to prevent mercury leakage and with a rectangular plastic carriage framework reciprocal within the housing to carry the silver and mercury from separate inlet ports to the funnel for mixing. The carriage includes a pair of rails lying on either side of the inlet and outlet ports to prevent twisting of the carriage within the housing. A mercury reservoir is located atop the housing and is equipped with a micropore filter which prevents the formation of a vacuum in the reservoir chamber. The fineness of the openings in the filter at the same time prevents the passage of mercury therethrough.

7 Claims, 6 Drawing Figures

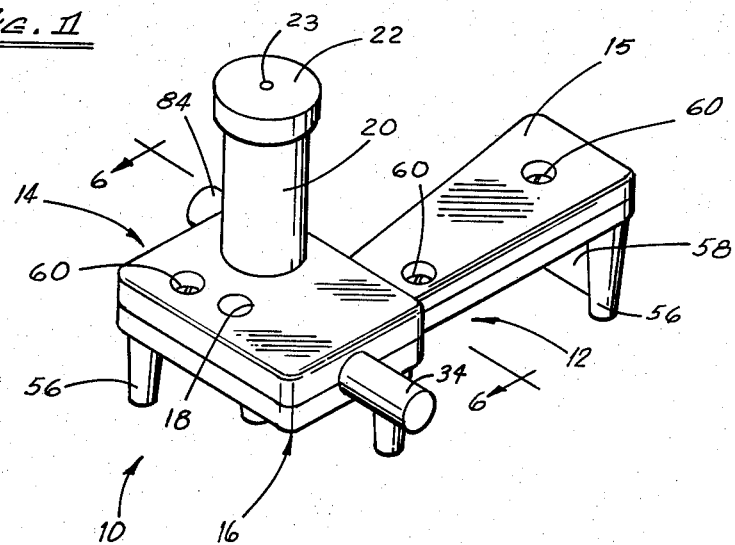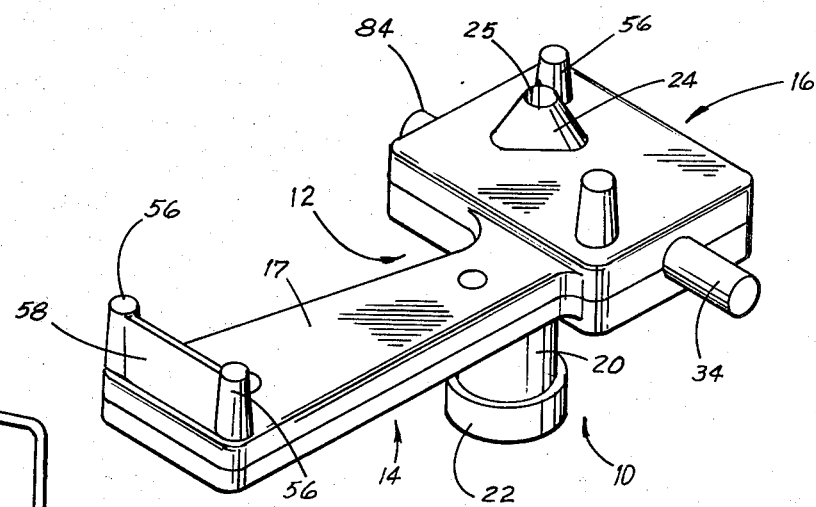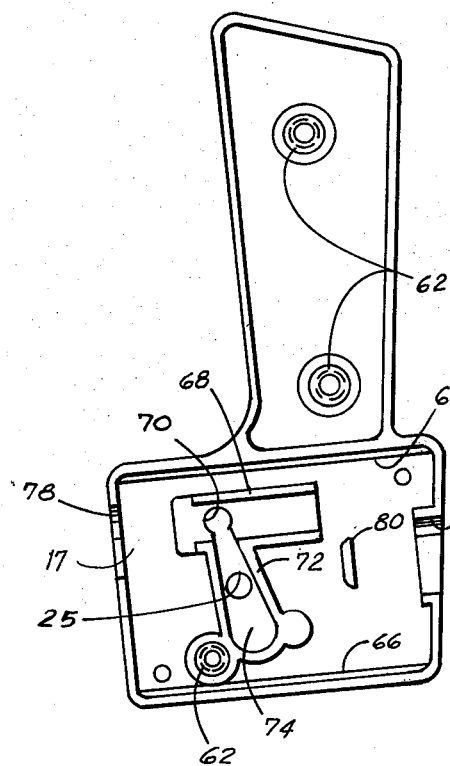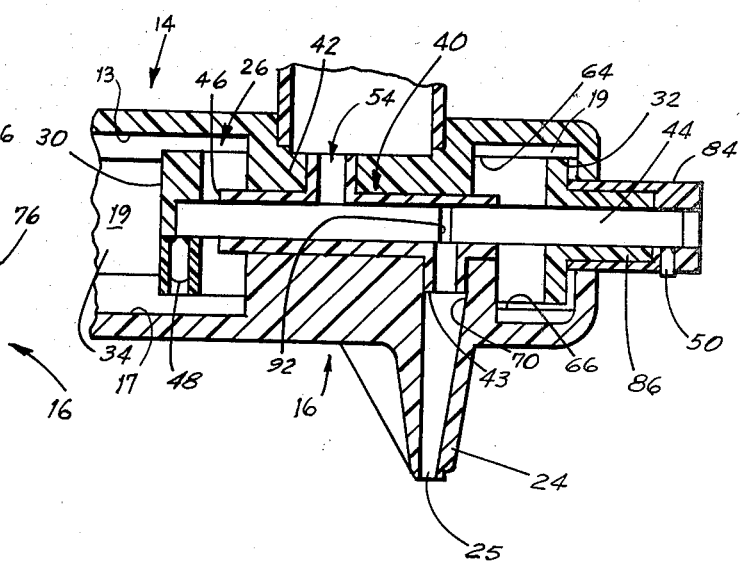

DENTAL AMALGAM DISPENSER

BACKGROUND OF THE INVENTION

1. Field of the Invention

The present invention relates to devices for dispensing mercury and silver in measured proportions for mixture to form a dental amalgam.

2. Description of the Prior Art

A considerable number of devices have been devised for use in dispensing mercury and silver to form dental amalgams. One prior art device is described in U.S. Pat. No. 3,168,213. In the dispenser described therein, a rectangular carriage is spring biased to a position to accept measured aliquots of mercury and silver in two different inlets, and to dispense these materials for mixing into a funnel glued to the bottom of the dispenser housing. However, in this device one of the slidable legs of the rectangular carriage is formed by a steel slide having a tray therein, open at the top and bottom. The steel slides within the plastic housing to carry a tablet disk of silver to the funnel. The other parallel sliding member of the carriage is a steel rod which slides within a sleeve to receive mercury and dispense it into the funnel. With this construction, the device is subject to the application of excessive torque, as a manual pressure can be applied anywhere across a transverse push bar which joins the sliding, parallel carriage members. The carriage is manually operated in reciprocal fashion by the thumb of a person's hand when a handle on the housing is held in the palm of the hand. Considerable torque will be applied to one or the other or both of the sliding members depending upon the position of the thumb on the transverse push bar at the end of the carriage. The torque developed is further magnified, because the sliding carriage members function also as the guiding elements in movement of the carriage relative to the housing. This contributes greatly to wear on the housing, since the reciprocating steel slide wears against the plastic housing in its sliding movement, especially when torque is applied. Moreover, because of the application of torque and excessive wear, precise control of the quantity of mercury dispensed is difficult.

Additionally, because the body of the housing is formed from a unitary plastic structure, it is necessary for the funnel to be separately attached to the housing body. This attachment is by means of glue, and the joints between the funnel and the housing are frequently imperfect. As a result, the device is susceptable to leaks around the interface between the funnel and the housing. All of the foregoing defects lead to a shortened longevity of the dispenser.

Another prior art device is depicted and described in U.S. Pat. No. 3,347,530. This functions in a fashion similar to the foregoing prior art devices described herein, but with the exception that the slide member carrying the silver tablet is constructed of plastic. This decreases the rapid wear of the slide relative to the plastic of the housing, but introduces a tendency for the plastic portion of the carriage to bind within the housing.

A characteristic feature of all of the foregoing types of dental amalgam dispensers is that the sliding carriage members also serve as the transport members for carrying the silver and mercury to an attached funnel. Because it is necessary for the inlets for the silver and the mercury to be located proximate to each other for mixing in the funnel, this type of construction as heretofore been accepted by manufacturers of dental amalgam dispensing devices, despite the high degree of torque and attendant wear that results from the close proximity of the sliding carriage members.

SUMMARY OF THE INVENTION

It is an object of the present invention to provide a dental amalgam dispenser in which wear between the carriage and the housing through which the carriage passes is remarkably reduced. This wear reduction is achieved by providing the carriage with separate parallel side rails that ride within tracks in the housing. The side rails are well displaced from both the silver inlet port and the mercury inlet port. That is, the slide rails straddle these inlet ports on either side thereof. A centrally located carriage actuator is provided to bear directly against a transverse push bar of the carriage midway between the two slide rails. The application of force along a line midway between and parallel to the slide rails substantially decreases the torsional forces developed between the carriage and the housing. Moreover, because of the reduction of torsional forces, the carriage can be built entirely of molded plastic, which leads to economy in construction and also elimination of the wear of metal carriage guides against the plastic structure of the housing. As a consequence, the amalgam dispenser remains servicable for extended periods of time when contrasted with conventional devices.

The housing of the dispenser of the invention is not constructed of a unitary hollow body. Rather, it is formed of upper and lower discrete components, each of separate unitary construction. This allows the outlet funnel to be integrally formed with the lower housing component. The two components are fastened together along a generally horizontal demarkation. Fastening may be by adhesive, but preferably is performed with machine screws. By forming the funnel in integral fashion with the lower portion of the housing component, a source of mercury leakage on the underside of the housing at the junction between the funnel and the housing is eliminated.

Preferably, the device of the invention is constructed with a micropore filter fixed to the inside of a removable vented cap on the mercury reservoir. A micropore filter allows the passage of air, thereby preventing the formation of a vacuum in the mercury reservoir so that mercury is free to flow downward. At the same time, the pores of the micropore filter are to small to allow passage of mercury, which is quite cohesive. As a consequence, the mercury will remain in the reservoir, even if the dispenser is inverted and the mercury comes into contact with the micropore filter.

The particular structure and advantages of the device of the invention are illustrated with greater clarity and particularity by reference to the accompanying drawings.

DESCRIPTION OF THE DRAWINGS

FIG. 1 is a perspective view of one embodiment of the dental amalgam dispenser of the invention.

FIG. 2 is a perspective view of the underside of the embodiment of FIG. 1.

FIG. 3 is a plan view of the lower housing component of the dispenser.

FIG. 6 is a sectional elevational view taken along the lines 6–6 of FIG. 1.

DESCRIPTION OF THE EMBODIMENT

Figure 4:
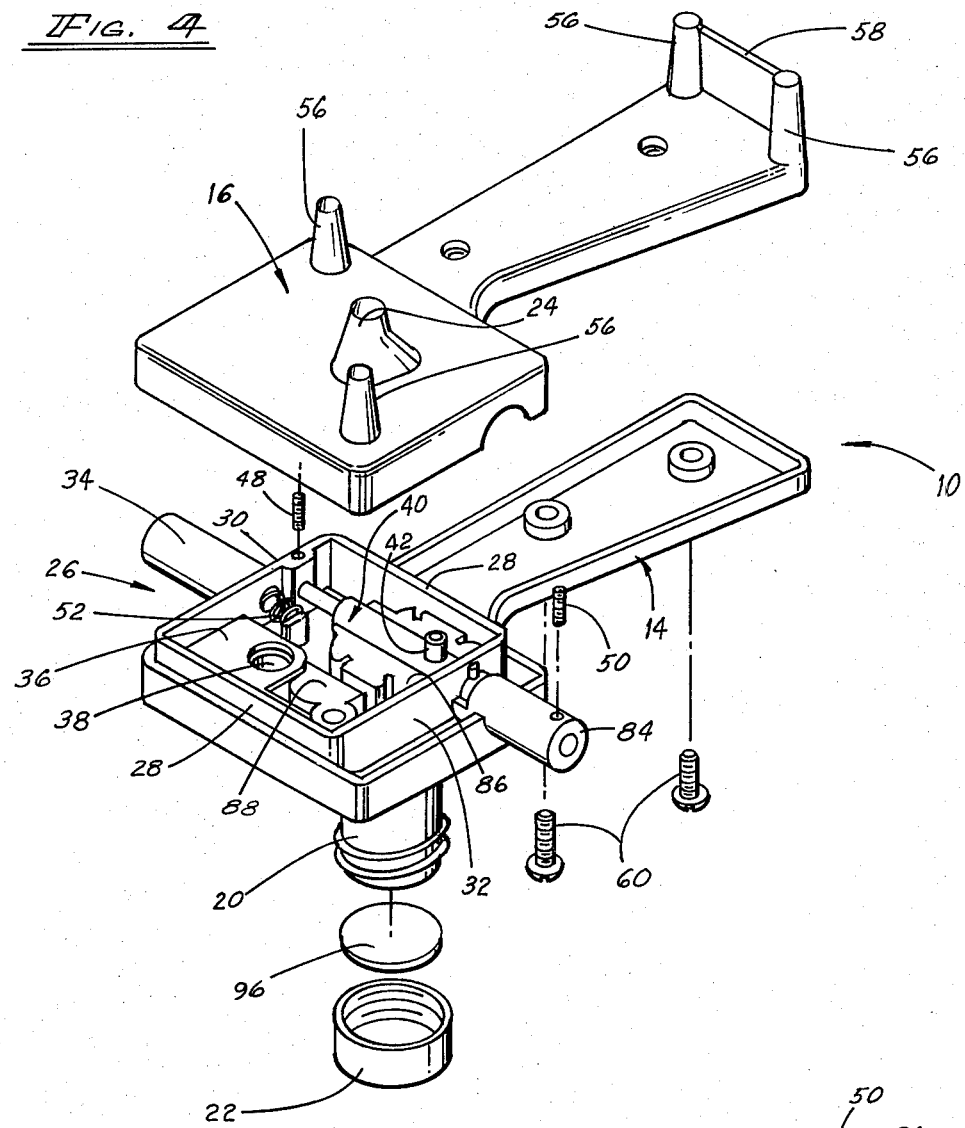
FIG. 4 is an exploded view of the dispenser in an inverted orientation.

With reference to FIG. 1, a dispenser 10 is provided for expelling aliquot quantities of liquid mercury and tablets of ground silver for mixture into a composite amalgam. The dispenser 10 includes a housing 12 which has a bifurcated unitary upper component 14 and a unitary lower component 16. The upper component 14 has an internal roof 13, visible in FIGS. 4–6 and includes a downwardly extending inlet port 18 which receives vertically stacked disk shaped tablets of silver one at a time. The upper component 14 also includes a inlet port 54 for the liquid mercury, visible in FIG. 6. The mercury is retained within an upstanding cylindrical reservoir tank 20 having a cap 22 sealed at the upper extremity thereof. The cap 22 is vented by an aperture 23. The lower component of the housing 12 has an internal floor 17, visible in FIGS. 3 and 6, and is equipped with an integrally formed funnel 24, visible in FIG. 2, for receiving both the mercury and the silver and for directing these materials to a single outlet port at the lower extremity of the funnel, indicated at 25. Together the housing components 14 and 16 define a hollow enclosure 19, indicated in FIG. 6.

Figure 5:
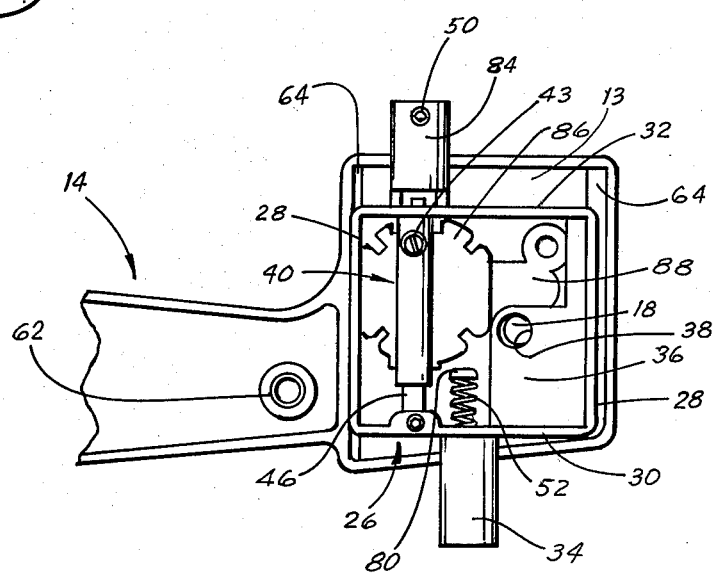
FIG. 5 is a partial plan view from beneath the upper housing component showing the carriage therein and with the lower housing component removed.

As depicted in FIGS. 4 and 5, the dispenser 10 is equipped with a carriage 26 which has a rectangular framework including lateral side rails 28 and interconnecting transverse ends 30 and 32. The carriage reciprocally moves within the confines of the housing 12 by means of a hollow cylindrical actuating post 34 which is closed at its exposed end and which extends outwardly through an opening in the housing from the carriage 26. A compressed coil spring 52, extending into the hollow enclosure formed within the actuating post 34, biases the carriage relative to the housing 12 and pushes the actuating post 34 outward. A platelike slide 36 is connected to the end wall 30 and one of the side rails 28, as depicted in FIGS. 4 and 5, to carry silver tablets in a tray defined by a circular aperture 38 formed therein from the inlet port 18 of FIG. 1 to registration directly above the funnel 24. The carriage 26 also includes a cylindrical, annular guide collar 86 which extends outwardly from the housing 12 and is received within the hollow guide sleeve 84, as depicted in FIG. 6.

The dispenser 10 is also equipped with a cylindrical annular transport tube 40, depicted in FIGS. 4 and 5 and 6, disposed parallel to and between the side rails 28. The transport tube 40 has an upwardly directed inlet collar 42, visible in FIG. 6, in registration with the inlet port 54 from the mercury reservoir tank 20 and a downwardly directed downspout 43 which resides directly above the funnel 24. A plunger is reciprocal within the transport tube 40. The plunger is formed by a pair of coaxial rods 44 and 46, longitudinally separated by a gap 92, which are fastened to the carriage 26 by means of transversely directed allen head set screws 48 and 50.

The housing 12 is formed of two concave components 14 and 16. The components 14 and 16 are integrally molded plastic pieces which fit together as indicated in FIGS. 1 and 2. The components 14 and 16 include elongated handle sections 15 and 17, which broadens slightly at their free ends. At the opposite ends of the handle sections 15 and 17, the housing 12 terminates in a trapezoidal shaped section containing the inlet and outlet ports. The underside of the lower component 16 includes downwardly depending feet 56 and the funnel 24, visible in FIG. 2. The feet 56 at the handle end of the lower component 16 are joined together by a thin partition 58. The feet 56, the partition 58 and the funnel 24 are all integrally formed as part of the lower section 16. As a consequence, there is no joint between the funnel 24 and the undersurface of the lower component 16 through which mercury can leak. The upper and lower components 14 and 16 are joined together by means of machine screws 60, as indicated in FIG. 4 which are threadably engaged in brass bushings 62, visible in FIGS. 3 and 5. The brass bushings 62 are secured in molded recesses in the interior of the lower component 16. The upper and lower components 14 and 16 are thereby held in releasable fashion, tightly engaged to entrap the rectangular framework formed by the side rails 28 and the end walls 30 and 32 of the carriage 26.

The side rails 28 slide along molded ledges 64 and 66, defined in the upper and lower components 14 and 16 of the dispenser housing and depicted in FIGS. 3,5 and FIG. 6. The ledges 64 and 66 together define tracks, along which the side rails 28 slide. On the inside of the trapezoidal cavity formed in the lower component 16 of the dispenser housing 12, there is a longitudinal generally semicircular shaped cradle 68 extending parallel to the ledges 66. Towards one end of the cradle 68 there is defined a downwardly depending well 70 with sloping sides which partially forms the funnel 24 and which leads to the outlet 25 of the funnel 24 at the apex thereof. The well 70 serves to conduct mercury through the funnel 24 to the outlet 25.

Displaced from the cradle 68, there is a wall 72 which extends about an enlarged opening 74 and which transversely intersects the cradle 68. The opening 74 likewise has sloping walls and leads to the outlet 25 at the funnel apex. Tablets of silver drop into the opening 74 and are conducted to the outlet 25 for mixing with the mercury for expulsion from the dispenser 10 as an amalgam.

With reference to FIG. 3, the opposing ends of the trapezoidal cavity defined within the lower component 16 include an opening 76 adapted to receive the carriage acuating post 34, and an opening 78 adapted to receive a carriage guide sleeve 84. A spring support post 80, standing within the cavity and displaced from the opening 76, meets and co-operates with a similarly located spring support post 80 in the cavity of the upper compartment 14 to provide a bearing anchor so that the spring 52 is able to bias the carriage 26 to allow admission of the silver and mercury into the inlet ports 18 and 54 respectively. The spring support posts 80 also limit the reciprocal movement of the carriage 26.

The upper component 14 likewise includes openings to receive the carriage actuating post 34 and the carriage guide 84, as depicted in FIG. 5. In addition, the upper component 14 also includes in its trapezoidal cavity a channeled support block 86 with a channel of semicircular cross section defined therein parallel to the ledges 64. Adjacent to the support block 86 there is an irregular shaped guide block 88 which is stepped down from the support block 86 to accomodate the passage of the slide 36 of the carriage 26. The silver inlet port 18, depicted externally in FIG. 1, appears at the interior of the upper component 14 through an aperture in the guide block 88 under the normal bias of the spring 52. The aperture 38 in slide 36 is moved into alignment with the opening 74 of the funnel 24 in the lower component 16 when the carriage actuator 34 is pushed inward to its extreme position where the end wall 30 abuts the spring support posts 80. Movement in this fashion overcomes the bias of the compressed coil spring 52. At the same time, the plunger mechanism which includes the coaxial plunger rods 44 and 46 is moved so that the gap therebetween, indicated at 92, lies directly above the well 70 of the funnel 24. The plunger rods 44 and 46 move within the transport tube 40 between opposite extreme positions in which the gap 92 therebetween is aligned with the downwardly depending downspout 43 of the transport tube 40 as depicted in FIG. 6, and an opposite position in which the gap 92 is aligned with the inlet collar 42.

The width of the gap 92 may be altered by loosening either the set screw 48 or the set screw 50 and shifting the corresponding plunger rod 46 or 44 longitudinally along the common axis and then retightening the set screws. In addition to providing means for adjustment, the set screws 48 and 50 secure the plunger rods 44 and 46 to the carriage 26 so that the location of the gap 92 within the transport tube 40 is determined by movement of the carriage actuating post 34. Also, the set screw 50 causes the guide sleeve 84 to move as part of the carriage 26.

The mercury reservoir tank 20 is positioned within a circular depression within the top surface of the upper housing component 14. The cylindrical tank 20 is equipped with a cap 22 which is threadably engagable therewith, and which also includes a disk shaped micropore filter 96, indicated in the exploded view of FIG. 4. The pores of the micropore filter 96 are large enough to allow the passage of air, and thus prevent a vacuum from forming above mercury in the tank 20. Air is drawn in through the aperture 23. The pores of micropore filter 96 are too small, however, to allow mercury to escape the tank 20, should the dispenser be inverted to the position of FIG. 4.

In the operation of the invention, release of the carriage actuator 34 allows the compressed coil spring 52 to push the carriage 26 so that the aperture 38 in slide 36 is brought into registration with the inlet port 18 in the dispenser housing 12. Concurrently, the plunger rods 46 and 44 are carried with the carriage 26 so that the gap 92 aligns with the mercury inlet port 54 and the inlet collar 42. A small drop of mercury of a volume determined by the volume of the gap 92 fills the gap and is ready for expulsion. By the same token, the bottom tablet of silver in a stack of tablets above the inlet port 18 moves into registration with the aperture 38 in slide 36.

Pressure may be exerted on the carriage actuating post 34 by manually grasping the handle 15 of the housing 12 with the right hand and exerting pressure upon the end of the carriage actuator 34 with the ball of the right thumb. Inward pressure on the carriage actuator 34 carries the carriage from a position in which the slide aperture 38 is in registration with the inlet port 18 and the gap 92 is in registration with the mercury inlet port 54, to a position in which the slide aperture 38 is in registration with the opening 74 and the gap 92 is in registration with the well 70, as depicted in FIG. 6. In this position, the drop of mercury in the gap 92 is free to fall through the downspout 43, into the well 70, where it is channeled through the funnel 24 to the outlet 25 therefrom. Concurrently, the disk shaped pellet of silver drops into the opening 74 and likewise is carried to the outlet 25 of the funnel 24. At the outlet 25 the aliquots of silver and mercury first meet and are discharged for thorough mixing. Release of pressure from the carriage actuator 34 allows the biasing spring 52 to return the carriage 26 to its original position.

The mercury within the reservoir tank 20 is able to fill the gap 92 because a vent is provided through the aperture 23 in cap 22, and through the pores of the micropore filter 96. Nevertheless, mercury cannot leave the reservoir tank 20. As a consequence, the mercury can be safely and conveniently stored in the reservoir 20, without fear of spilling or leakage. The small pore size of the micropore filter 96 prevents the mercury from being spilled, while the integral formation of the funnel 24 with the lower component 16 of the housing 12 prevents mercury from leaking at the base of the funnel 24.

Depending upon the amount of amalgam required, one or more aliquots of mercury and silver are dispensed through the outlet port 25. To dispense sequential aliquots, pressure is merely applied and released on the carriage actuator 34 a number of times equal to the number of units of amalgam required. As previously noted, while the set screws 48 and 50 are not normally altered once a requisite volume in the gap 92 is defined, it is possible to alter this volume if desired. As previously noted, this is done by loosening one of the set screws 48 or 50, moving the corresponding plunger rod 44 or 46, and retightening the set screw.

Undoubtedly, numerous varations and modifications of the invention will be considered by those skilled in the art. Accordingly, the scope of the invention should not be limited to the specific embodiment depicted in the drawings, but rather is defined in the claims appended hereto.

We claim:

1. A dispenser for liquid mercury and silver for mixture in an amalgam comprising:
   a bifurcated plastic housing constructed of upper and lower discrete concave components, each of unitary construction, said upper component having separate inlet ports for mercury and silver and said lower component having an integrally formed funnel for receiving both mercury and silver and for directing both said mercury and said silver to a single outlet port, said upper and lower components respectively having a roof and a floor and together defining a hollow enclosure within said housing, wherein said housing is formed with a pair of parallel spaced tracks on opposite sides thereof laterally bracketing said inlet ports and said outlet port and said funnel,
   a plastic carriage having an open rectangular frame with opposing side rails disposed to ride in reciprocating movement along said tracks and opposing transverse ends, and said carriage is movable entirely 2. A dispenser according to claim 1 further characterized in that said plunger means includes axially aligned rods with a gap therebetween coupled to opposite sides of said framework, whereby said gap between said rods is movable from registration with said inlet to registration with said funnel.

3. A dispenser according to claim 2 further characterized in that at least one of said rods is longitudinally adjustable relative to said frame to vary the width of said gap.

4. A dispenser according to claim 1 further characterized in that said housing includes a handle for grasping.

5. A dispenser according to claim 1 further comprising a vented mercury reservoir positioned above said mercury inlet port in said housing and including a micropore filter, the pores of which prevent the formation of a vacuum and prohibit the passage of mercury therethrough.

6. A dispenser according to claim 1 further characterized in that said slide, said carriage actuator and said framework are integrally constructed of molded plastic.

7. A dispenser according to claim 6 further characterized in that said upper and lower housing components are each integrally constructed of molded plastic.

* * * * *

UNITED STATES PATENT AND TRADEMARK OFFICE
CERTIFICATE OF CORRECTION

PATENT NO. : 4,228,919

DATED : October 21, 1980

INVENTOR(S) : Maurice M. Weikel

It is certified that error appears in the above-identified patent and that said Letters Patent are hereby corrected as shown below:

Please amend the above Patent as follows:

In the drawings in Fig. 2 please place a --'-- by the reference number 17.

In Fig. 6 please relocate the designation for the hollow enclosure 19 from a position superimposed upon the actuating post 34 to a position therebeneath.

In the specification at column 2, line 50 delete "to" first occurrence, and insert -- too --.

At column 3, line 17 delete "a" and insert --an--.

At column 6, line 58 insert the following after "entirely" --, within the hollow enclosure defined in said housing,

UNITED STATES PATENT AND TRADEMARK OFFICE
CERTIFICATE OF CORRECTION

PATENT NO. : 4,228,919
DATED : October 21, 1980
INVENTOR(S) : Maurice M. Weikel

It is certified that error appears in the above-identified patent and that said Letters Patent are hereby corrected as shown below:

a cylindrical carriage actuator connected to said frame and protruding through said housing only at a location midway between said side rails and spaced from said housing roof and floor, a plastic slide within said housing laterally offset from said carriage actuator and coupled to said carriage frame between said side rails and spaced from said housing roof and said floor for carrying silver parallel to said side rails from said silver inlet port to said funnel for dispensation, a lateral mercury transport tube located between said transverse carriage ends and parallel to said side rails

UNITED STATES PATENT AND TRADEMARK OFFICE
CERTIFICATE OF CORRECTION

Page 3 of 3

PATENT NO. : 4,228,919
DATED : October 21, 1980
INVENTOR(S) : Maurice M. Weikel

It is certified that error appears in the above-identified patent and that said Letters Patent are hereby corrected as shown below:

and laterally offset from said carriage actuator and spaced from said roof and said floor and having an inlet in registration with said mercury inlet port of said housing and an outlet in registration with said funnel, plunger means in axial alignment with said mercury transport tube and connected to said frame between said side rails and offset from said actuator and reciprocal within said transport tube for carrying a measured quantity of mercury from said mercury inlet to said funnel, and spring biasing means for biasing said framework to a predetermined position along said housing track--

Signed and Sealed this

Twenty-sixth Day of May 1981

[SEAL]

*Attest:*

RENE D. TEGTMEYER

*Attesting Officer*    *Acting Commissioner of Patents and Trademarks*